United States Patent [19]
Pinza et al.

[11] Patent Number: 4,868,313
[45] Date of Patent: Sep. 19, 1989

[54] A PROCESS FOR MAKING PYRROLIDONE DERIVATIVES

[75] Inventors: Mario Pinza, Milan; Carlo Farina, Como; Silvano Banfi; Ugo Pfeiffer, both of Milan, all of Italy

[73] Assignee: I.S.F. Societa Per Azioni, Milan, Italy

[21] Appl. No.: 300,526

[22] Filed: Jan. 23, 1989

Related U.S. Application Data

[60] Division of Ser. No. 131,862, Dec. 11, 1987, Pat. No. 4,824,861, which is a continuation of Ser. No. 876,492, Jun. 20, 1986, abandoned.

[51] Int. Cl.$^4$ .......................................... C07D 207/327
[52] U.S. Cl. ................................. 548/544; 548/351
[58] Field of Search ......................................... 548/544

Primary Examiner—David B. Springer
Attorney, Agent, or Firm—Nancy S. Mayer; Janice E. Williams; Alan D. Lourie

[57] ABSTRACT

The invention relates to 4-hydroxy pyrrolidone derivatives which help restore learning and memory difficulties associated with ageing. A compound of the invention is 2-(4-hydroxy-2-oxo-1-pyrrolidineacetamido)acetamide.

1 Claim, No Drawings

A PROCESS FOR MAKING PYRROLIDONE DERIVATIVES

This is a divisional of application Ser. No. 07/131,862 filed Dec. 11, 1987, U.S. Pat. No. 4,182,861, which is a continuation of Ser. No. 876,492 filed June 20, 1986, now abandoned.

This invention relates to new chemical compounds which have useful pharmacological activity, to processes and intermediates for making them, and pharmaceutical compositions containing them.

According to the invention we provide compounds of Structure (1)

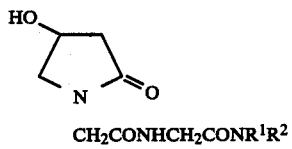

$CH_2CONHCH_2CONR^1R^2$ in which
$R^1$ is hydrogen or $C_{1-4}$ alkyl (straight or branched), and
$R^2$ is hydrogen or $C_{1-4}$ alkyl (straight or branched).

Examples of $C_{1-4}$ alkyl are methyl, ethyl, propyl, n-butyl, isobutyl and tertiary butyl.

Preferably $R^1$ is hydrogen.
Preferably $R^2$ is hydrogen.

It will be appreciated that the Structure (1) have a chiral centre at the carbon atom to which the hydroxy group is attached. The present invention covers all optical isomers of these compounds in their fully and partially resolved forms and in the form of racemic mixtures.

The compounds of Structure (1) can be prepared by the following general methods:

A. compound of Structure (2)

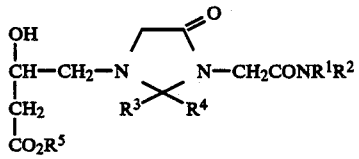

wherein $R^1$ and $R^2$ are hydrogen or $C_{1-4}$ alkyl (straight or branched), $R^3$ and $R^4$ are independently hydrogen, $C_{1-4}$ alkyl (straight or branched), phenyl, or $R^3$ and $R^4$ are taken together to be 1,4-butylene ($-(CH_2)_4-$) or 1,5-pentylene ($-(CH_2)_5-$), and $R^5$ is $C_{1-4}$ alkyl (straight or branched), is deprotected (i.e. the $R^3R^4C=$ group is removed) and the product is intramolecularly cyclised; or B. A pyrrolidone derivative of Structure (6)

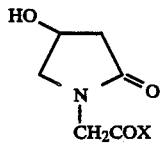

in which X is OH or a leaving group displaceable with an amine, is reacted with a glycinamide or a precursor thereof and if necessary converting the product in which X is a precursor of a glycinamide into a compound in which X is $NHCH_2CONR^1R^2$.

Preferably in the Compounds of Structure (2) $R^3$ is isopropyl and $R^4$ is hydrogen, or $R^3$ and $R^4$ are both methyl. Preferably $R^5$ is isobutyl as the precursor 3,4-epoxybutanoate ester of Structure (4) is convenient to handle.

Deprotection and intramolecular cyclisation of the compounds of Structure (2) can be effected by heating in the presence of water at temperatures between 90° and 160° C., preferably between 100° and 130° C.. It is convenient to use water or mixtures of solvents and water. Preferably the solvent is a 95% mixture of an organic solvent with water (5%). As organic co-solvents may be used dimethylformamide (DMF), dimethylsulphoxide (DMSO), dimethylacetamide (DMA), acetonitrile and alcohols such as ethanol, etc. Preferably the reaction is carried out in the presence of a carboxylic acid, e.g. acetic acid or benzoic acid. Although catalytic quantities of carboxylic acids are effective, preferably 0.8 to 1.2 molar equivalent of a carboxylic acid is used.

The compounds of Structure (2) can be prepared by reacting a compound of Structure (3) with a 3,4-epoxybutanoate ester of Structure (4).

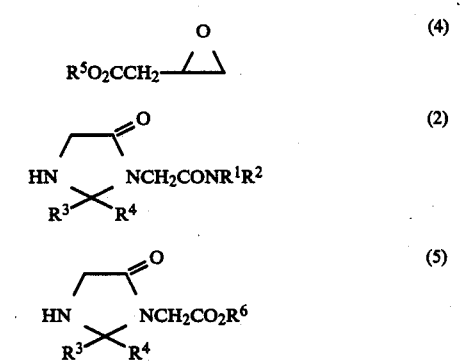

The compounds of structure (3) can be prepared by reacting an ester of Structure (5) where $R^3$ and $R^4$ are as defined for Structure (2) and $R^6$ is $C_{1-4}$ alkyl (straight or branched) with an amine of structure $NHR^1R^2$. The compounds of Structure (4) can be prepared as described in EPA No. 0154490 (ISF).

The reaction between the compounds of Structures (3) and (4) may take place without the use of solvents or in the presence of organic solvents, water or aqueous mixtures of these in proportions of from 1:5 to 20:1, preferably from 1:1 to 1:3 of organic solvent and water. As organic solvent may be used a wide variety of polar or non-polar solvents e.g. acetonitrile, alcohols such as isopropanol and pentanol, and ketones such as acetone. The reaction is performed at a temperature of 20° to 120° C., preferably 70-100° C. and the two reagents may be used in stoichiometric proportions, or an excess of one of them may be used, preferably a ratio of from 1:1 to 1:1.1 of the imidazolidinone (3) and the epoxyester (4).

The compounds of Structure (5) can be prepared from the salts of the corresponding acids described by Panetta et al. J.Org.Chem. 37 302 (1972), and methods analogous to those described by Panetta et al.

One precursor of glycinamide is 2-isopropyl imidazolidin-4-one, other precursors are other cyclic imidoacetal and imidoketal derivatives.

For the compounds of Structure (6) examples of leaving groups X which are displaceable with an amine are $C_{1-4}$ alkoxy, amino ($NH_2$) and azido ($N_3$) (which can be prepared for example by reacting a hydrazide with an alkyl nitrite). When X is OH this group will require activation, for example conversion into an acid chloride, acid azide, an acid anhydride (e.g. by reaction with an alkyl chloroformate or pivaloyl chloride), an activated ester or the use of a peptide coupling agent.

It will be appreciated that the activation of the carboxyl group might necessitate the temporary protection of the hydroxy group. Suitable hydroxy protecting groups, activated esters and peptide coupling reagents are well known and are described for example in 'Peptide Synthesis' by M. Bodansky, Y. Klausner and M. Ondetti (Wiley 1976) or Protective Groups in 'Organic Chemistry' by T. W. Greene (Wiley 1981). Examples of hydroxy-protecting groups are tetrahydropyranyl, trimethylsilyl, benzyl and t-butyl.

Examples of activated esters are trichlorophenyl, pentachlorophenyl, N-hydroxysuccinimido and 1-hydroxybenzotriazole esters. Examples of peptide coupling reagents are carbodiimides (such as N,N'-dicyclohexylcarbodiimide), N,N'-carbonyldiimidazole, 1-ethoxycarbonyl-2-ethoxy-1,2-dihydroquinoline (EEDQ), and isoxazolium derivatives such as N-ethyl-5-phenylisoxazolium-3'-sulphonate (Woodward's Reagent K).

The solvent chosen for the reaction will depend on the solubility of the reactants and their reactivity. For example when X is $NH_2$ or $C_{1-4}$ alkoxy the reaction may be carried out in an alkanol or in an aqueous mixture of an alkanol, for example aqueous amyl alcohol. When the carboxyl group requires activation then the reaction will normally be carried out in a dipolar aprotic solvent such as tetrahydrofuran, dioxane, dimethoxyethane or dimethylformamide.

Preferably X is methoxy or ethoxy and the compound of Structure (6) is reacted with glycinamide.

The intermediates of Structure (2) and (3) are novel compounds and form important aspects of the invention.

The compounds of Structure (1) have useful nootropic activity, that is they help restore learning and memory difficulties associated with ageing and various pathologies including Alzheimer's disease. The present invention therefore provides, is a further aspect of a method of restoring learning and treating memory difficulties which comprises administering to a mammal in need thereof a non-toxic effective amount of a compound of Structure (1). The cognitive disorders occurring in such pathologies are known to be related to deficits in the brain cholinergic system as shown both by morphological (B. E. Tomlinson in "Biochemistry of Dementias"; P. J. Roberts Ed.; John Wiley & Sons, New York, N.Y. p. 15–22, 1980) and Neurochemical Finiings (R.T. Bartus et al., Science, 217, 408, 1982). It is also well known that significant impairments of cognitive functions are the more evident and debilitating symptoms observed in patients with Alzheimer's disease, senile dementia of the Alzheimer type and multiinfarctual dementia. On the other hand, the anticholinergic drug scopolamine, produces in humans (D. A. Drachman, Archs. Neurol., Chicago, 30, 113, 1974) as well as in animals (D. A. Eckerman, Pharmacol. Biochem. Behav., 12, 595, 1980) a significant memory loss, which is directly related to a decrease of acetylcholine concentration in specific cerebral areas such as the cerebral cortex and the hippocampus. On the basis of these premises, compounds of structure 1 have been specifically tested in rats against both the disruptive action of scopolamine on amnestic trace and on the reduction of acetylcholine levels in hippocampus. To evaluate the effect on memory and learning, one trial-step through-passive avoidance test in male Wistar rats (150–160 g) was used. The equipment was essentially the ssame described by Essman (Pharmacol. Res. Commun, 5, 295, 1973).

The passage from a light box into a dark one was punished by unavoidable electric foot shocks. The animals must learn to avoid, after a single learning session, the crossing from the light to the dark box. Thirty minutes after the first session (learning session), the learning effect was quantified (retest session) by means of the latencies (in seconds) between the admission of animals into the light box and the entering into the dark one. The learning effect is substantially impaired by a treatment with scopolamine (0.63 mg/kg i.p.) sixty minutes before the learning session. Saline or the test compounds were administered i.p. thirty minutes before scopolamine. The control group was treated in the same way but with saline only. For example, results on compound A (1, $R^1=R^2=H$) are given in Table 1.

TABLE 1

Activity of compound A on the learning impairment caused by scopolamine (0.63 mg/kg i.p.) in rat

| Treatment[a] | Dose mg/kg ip | Latencies (seconds)[b] | | |
|---|---|---|---|---|
| | | Learning session | Retest session | difference |
| Saline | — | 23.06 | 129.20 | 106.14** |
| Scopolamine | — | 26.04 | 36.09 | 10.5 |
| A + Scopolamine | 100 | 25.41 | 92.01 | 66.60* |
| A + Scopolamine | 300 | 28.00 | above 150 | above 122** |

[a]Five rats were used for each experimental group
[b]Cut off time: 150 seconds
*Dunnet's test: p less than 0.05
**Dunnt's test: p less than 0.001

To evaluate the acetylcholine levels in hippocampus the methods of Jenden et al., (in "Choline and Acetylcholine: Handbook of Chemical Assay Methods", I. Hanin Ed., Raven Press, pp. 135–150, 1974) was used on Wistar rats. Animals were with saline or test compound thirty minutes before scopolamine (0.63 mg/kg i.p.). The control group was treated in the same manner with the respective vehicles. Ninety minutes after administration of scopolamine, rats were killed by microwave irradiation; the hippocampus was dissected out of the brain and homogenized in 0.4N perchloric acid. To the clear supernatant obtained after centrifugation, butyrylcholine (internal standard) and potassium acetate were added in sequence. After further centrifugation, tetramethylammonium chloride and ammonium reineckate (Reinecke salt) were added to samples in order to precipitate acetylcholine. The precipitated pellets were treated as described (Jenden et al, ibidem). At the end the samples were extracted with 0.1 ml of ethyl acetate; 1 ml of the samples was injected in a HP Sigma 3B gas chromatograph equipped with a nitrogen-phosphorus detector.

For example, results on compound A (1, $R^1=R^2=H$ are given in Table 2.

TABLE 2

Activity of compound A on the reduction of acetylcholine (Ach) levels induced by scopolamine (0.63 mg/kg i.p.) in rat hippocampus

| Treatment[a] | Dose mg/kg i.p. | Ach levels nmoles/g | difference versus scopolamine |
|---|---|---|---|
| Saline | — | 21.68 | 12.87** |
| Scopolamine | — | 8.81 | — |
| A + Scopolamine | 100 | 18.10 | 9.29* |
| A + Scopolamine | 300 | 21.04 | 12.23** |

[a] Five rats were used for each experimental group
*Dunnet's test: p less than 0.01
**Dunnet's test: p less than 0.001.

It is surprising that Compound A would have such good activity in view of its polar and hydrophilic substituents which reduce its bioavailability.

In order to use a compound of Structure (1) for the therapeutic treatment of humans and animals, it will normally be formulated in accordance with standard pharmaceutical practice as a pharmaceutical composition. Therefore in another aspect the present invention provides a pharmaceutical composition which comprises a compound of Structure (1) and a pharmaceutically acceptable carrier.

The compounds of the Structure (1) may be administered in standard manner for the treatment of the indicated diseases, for example orally, parenterally, rectally, trans-dermally or by trans-mucosal (for example sub-lingual, or buccal or insufflatory) administration.

The compounds of the Structure (1) which are active when given orally or via sub-lingual or buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be utilised, for example aqueous gums, celluloses, silicates or oils and are incorporated in a soft gelatin capsule shell.

Typical parenteral compositions consist of a solution or suspension of the compound of the Structure (1) in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of Structure (1) which is active when administered in this way, with a binding and/or lubricating agent, for example polymeric glycols, gelatins, cocoa-butter or other low melting vegetable waxes or fats.

Typical transdermal formulations comprise a conventional aqueous or non-aqueous vehicle, for example a cream, ointment, lotion or paste or can be in the form of a medicated plaster, patch or membrane.

Preferably the composition is in unit dosage form, for example a tablet or capsule, so that the patient may administer to himself a single dose.

Piracetam is a compound which is used in the treatment of senile dementia and related disease conditions.

The compounds of Structure (1) can be administered in similar regimes to those established for piracetam with any appropriate adjustment in dose levels or frequency of dosing having regard to the greater activity and better pharmacological profile of the compounds of Structure (1).

Each dosage unit for oral administration contains suitably from 0.5 mg/Kg to 50 mg/Kg, and preferably from 1 mg/Kg to 8 mg/Kg, and each dosage unit for parenteral administration contains suitably from 0.1 mg/Kg to 10 mg/Kg, of a compound of Structure (1).

The daily dosage regimen for oral administration is suitably about 0.5 mg/Kg to 100 mg/Kg, more suitably about 1 mg/Kg to 25 mg/Kg of a compound of Structure (1). The active ingredient may be administered from 1 to 6 times daily. The compounds of Structure (1) may be co-administered with other pharmaceutically active compounds, for example in combination, concurrently or sequentially, particularly with other compounds used in the treatment of elderly patients e.g. tranquillisers, diuretics, antihypertensives, vasodilators and inotropic agents.

The invention is illustrated by the following Examples.

PREPARATION 1

2-Methylpropyl 3-carbamoylmethyl-Beta-hydroxy-2-(1-methylethyl)-4-oxo-1-imidazolidinebutanoate (1) To 50 ml of anhydrous ethanol stirred at 0°–5° C., 2 ml thionyl chloride were added. At the same temperature 2.1 g (0.01 mol) of sodium 2-(1-methylethyl)-5-oxo-1-imidazolidineacetate were added. The obtained suspension was stirred at 0° C. for 1 hour and at room temperature for 2 hours. The solvent was evaporated under reduced pressure and the residue taken up with ethyl acetate. The solid residue was filtered off and the solvent evaporated. The residue was dissolved in a saturated solution of sodium hydrogen carbonate and extracted with 3×50 ml of dichloromethane. The organic layers were evaporated to give ethyl 2-(1-methylethyl)-5-oxo-1-imidazolidineacetate (0.9 g) as a pale-yellow oil (42%) (Rf 0.6, ethyl acetate/dichloromethane 6:4; silica gel plates). Hydrochloride salt, m.p. 148°–149° C. (methanol/ethyl acetate).

(2) An ice cold solution of 3.8 g (0.018 mol) of ethyl 2-(1-methylethyl)-5-oxo-1-imidazolidineacetate in 100 ml of methanol was saturated with gaseous ammonia. The solution was stirred at room temperature overnight and the solvent was evaporated under reduced pressure, to give 2-(1-methylethyl)-5-oxo-1-imidazolidineacetamide (3.4 g) as a viscous oil (Rf 0.33; ethyl acetate/methanol 6:4; silica gel plates). Monohydrate of sulphate salt m.p. 64° C. resolidifying with final decomposition at 114°–118° C.

(3) A solution of 1.2 g (6.4 mmol) of 2-(1-methylethyl)-5-oxo-1-imidazolidineacetamide and 2 g of 2-methylpropyl 3,4-epoxybutanoate in 40 ml of anhydrous pentanol was stirred at 80° C. for 48 hours. The solvent was evaporated under reduced pressure. The residue was dissolved in 15 ml of 15% HCl, washed with 2×25 ml dichloromethane, basified with sodium carbonate with sodium carbonate and extracted with 3×35 ml dichloromethane. The organic layer was dried and evaporated to afford 1.08 g of the title compound as a colorless oil (mixture of two diastereoisomers, Rf 0.27 and 0.32 respectively (dichloromethane/methanol 9:1; silica gel plates). Mass spectrum (E.I., 70 eV, 1.5 mA), m/z=300 (M+—C$_3$H$_7$). IR spectrum (neat): 3400, 3200, 1730 and 1690 cm$^{-1}$.

PREPARATION 2

2-Methylpropyl 3-carbamoylmethyl-Beta-hydroxy2-(1-methylethyl)-4-oxo-1-imidazolidinebutanoate A solution of 1.91 g (0.01 mol) of glycylglycinamide acetate and 0.72 g (0.01 mol) of isobutyraldehyde in 40 ml of methanol was stirred for 24 hours at room temperature. The solvent was evaporated under reduced pressure and the residue was dissolved in 30 ml of isopropanol and treated with 0.106 g of sodium carbonate, 1.8 g (0.0115 mol) of 2-methylpropyl 3,4-epoxybutanoate and 2 drops of water. The mixture was refluxed for 36 hours. After evaporation of the solvent the residue was chromatographed on a silica gel column, eluting with dichloromethane/methanol 9:1. The title compound (0.48 g) was constituted by two diastereoisomers.

EXAMPLE 1

2-(4-Hydroxy-2-oxo-1-pyrrolidineacetamido)acetamide

A solution of 11.8 g (34.3mol) of 2-methylpropyl 3-carbamoylmethyl-Beta-hydroxy-2-(1-methylethyl)-4-oxo-1-imidazolidinebutanoate in 90 ml of dimethylformamide and 10 ml of water was gently refluxed (external temp. 130° C.) for 24 hours. The solvent was evaporated under reduced pressure. The oily residue was taken up with 40 ml of ethanol and stirred at 0° C. for 30 minutes. The precipitate was collected and crystallized from ethanol/isopropanol 1:1 to give 2.5 g of the title compound as a white powder, m.p. 158°-160° C. Mass spectrum (E.I., 70 eV, 1.5 mA), m/z=197 (M+—H$_2$O), 180. IR spectrum (oil mull): 3420, 3320, 3220, 1680, 1655 and 1630 cm$^{-31}$.

EXAMPLE 2

2-(4-Hydroxy-2-oxo-1-pyrrolidineacetamido)acetamide

A mixture of ethyl 4-hydroxy-2-oxo-1-pyrrolidineacetate (0.5 g) and glycinamide (0.6 g) was stirred under nitrogen at 80° C. for 4 hours. After cooling, the mixture was chromatographed on a silica gel column, by eluting with dichloromethane/methanol 7:3, affording the title compound (250 mg).

EXAMPLE 3

2-(4-Hydroxy-2-oxo-1-pyrrolidineacetamido)acetamide

To an ice-cold mixture of 4-hydroxy-2-oxo-1-pyrrolidineacetic acid (1 g) and glycinamide (700 mg) in dimethylformamide (20 ml), dicyclohexylcarbodiimide (1.3 g) was added at once. Stirring was continued for 5 hours at room temperature, then the solvent was removed under vacuum. The residue was suspended in water (20 ml) and stirred for 30 minutes at room temperature. The insoluble material was filtered off and the filtrate evaporated to dryness. The residue was triturated with 2-propanol to yield the title compound (700 mg).

EXAMPLE 4

| Composition for 1 tablet | | |
|---|---|---|
| 2-(Hydroxy-2-oxo-1-pyrrolidine-acetamido)acetamide | 100 | mg |
| lactose | 100 | mg |
| corn starch | 80 | mg |
| talcum | 11.5 | mg |
| silicon dioxide | 4 | mg |
| magnesium stearate | 2.5 | mg |
| gelatine | 2.0 | mg |

For the manufacture of 1000 tablets, 100 g of active ingredient are mixed with 100 g of lactose and 70 g of corn starch. The mixture is moistened with an aqueous solution of gelatine and then granulated and dried. The granules are mixed with 10 g of corn starch, 11.5 g of talcum, 4.0 g of silicon dioxide and 2.5 g of magnesium stearate and the mixture is pressed into tablets each weighing 300 mg and having the active ingredient content of 100 mg. The tablets can have different shapes and breaking notches for finer adjustment of the dosage.

What is claimed is:

1. A process for preparing a compound of Structure (1)

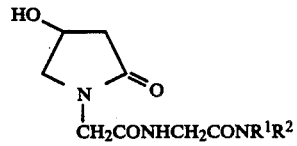

in which R$^1$ is hydrogen or straight or branched C$_{1-4}$ alkyl, and R$^2$ is hydrogen or straight or branched C$_{1-4}$ alkyl, which comprises:

Reacting a compound of Structure (6)

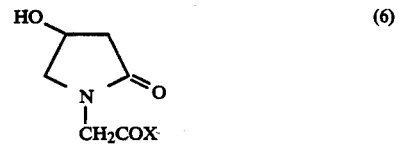

in which X is OH or a leaving group displaceable with an amine, with a glycinamide or a precursor thereof and if necessary converting the product in which X is a precursor of a glycinamide into a compound in which X is NHCH$_2$CONR$^1$R$^2$.

* * * * *